US010335476B2

(12) United States Patent
Thomas et al.

(10) Patent No.: US 10,335,476 B2
(45) Date of Patent: Jul. 2, 2019

(54) **VACCINE TO PROTECT AGAINST *EHRLICHIA* INFECTION**

(71) Applicants: Sunil Thomas, Dickinson, TX (US); David H. Walker, Galveston, TX (US)

(72) Inventors: Sunil Thomas, Dickinson, TX (US); David H. Walker, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/919,494

(22) Filed: Oct. 21, 2015

(65) Prior Publication Data

US 2016/0106825 A1    Apr. 21, 2016

Related U.S. Application Data

(60) Provisional application No. 62/066,461, filed on Oct. 21, 2014.

(51) Int. Cl.
*A61K 39/02* (2006.01)
*A61K 39/00* (2006.01)

(52) U.S. Cl.
CPC .... *A61K 39/0233* (2013.01); *A61K 2039/545* (2013.01); *A61K 2039/55566* (2013.01)

(58) Field of Classification Search
None
See application file for complete search history.

(56) References Cited

U.S. PATENT DOCUMENTS

| 5,582,829 | A | * | 12/1996 | Alliger | C12N 13/00 424/234.1 |
|---|---|---|---|---|---|
| 8,361,480 | B2 | | 1/2013 | Harrus et al. | 424/234.1 |
| 8,492,103 | B2 | | 7/2013 | Thomas | 435/7.32 |
| 8,685,406 | B2 | | 4/2014 | Walker | 424/190.1 |
| 9,151,755 | B2 | | 10/2015 | Walker | 424/190 |
| 2015/0313983 | A1 | * | 11/2015 | Rikihisa | A61K 39/0233 424/497 |

OTHER PUBLICATIONS

Mahan et al. (Onderstepoort Journal of Veterinary Research vol. 72, pp. 119-128).*
De Oliveira, et al., "Validation of an ELISA method for the serological diagnosis of canine brucellosis due to Brucella canis." Res Vet Sci. 90:425-31, 2011.
Mcbride and Walker, Expert Rev Mol Med. 13:e3, 2011.
Sutton, et al., "Therapeutic immunization against Helicobacter pylori infection in the absence of antibodies." Immunol and Cell Biol. 78:28-30, 2000.
Al-Oubaidy et al., "Immunopathological evaluation of the immunity induced by whole bacteria sonicated antigen of Brucella melitensis in guinea pigs," Al-Qadisiya J. Vet. Sci.-Supplement of 3rd conference, 2015, pp. 42-55.
Bolz et al., "Vaccination with the Surface Proteins MUL_2232 and MUL_3720 of *Mycobacterium ulcerans* Induces Antibodies but Fails to Provide Protection against Buruli Ulcer," PLOS Neglected Tropical Diseases 10(2): e0004431, 2016, 18 pages.
Johnson et al., "Antibodies to Pseudogymnoascus destructans are not sufficient for protection against white-nose syndrome," Ecology and Evolution, vol. 5, No. 11, 2015, pp. 2203-2214.
Melamed et al., "A vaccine against avian colibacillosis based on ultrasonic inactivation of *Escherichia coli*," Avian Diseases, vol. 35, No. 1, 1991, pp. 17-22.
Neilan et al., "Neutralizing antibodies to African swine fever virus proteins p30, p54, and p72 are not sufficient for antibody-mediated protection," Virology, vol. 319, 2004, pp. 337-342.
Sultana et al, "Control of Coccidiosis in Calves by Vaccination," J. Bacteriol. Parasitol., vol. 5, No. 4, 1000197, 2014, 5 pages.

* cited by examiner

*Primary Examiner* — Robert A Zeman
(74) *Attorney, Agent, or Firm* — Norton Rose Fulbright US LLP

(57) ABSTRACT

Certain embodiments are direct to a vaccine composition comprising an immunizing amount of an *Ehrlichia* sonicate, wherein the *Ehrlichia* sonicate elicits a protective physiologic response. In certain aspects the *Ehrlichia* is one or more of *E. canis, E. chaffeensis, E. muris, E. ruminantium, E. ewingii*, and *E. ovis*.

2 Claims, 4 Drawing Sheets

VACCINE TO PROTECT AGAINST *EHRLICHIA* INFECTION

This Application claims priority to U.S. Provisional Patent Application 62/066,461 filed Oct. 21, 2014, which is incorporated herein by reference in its entirety.

STATEMENT REGARDING FEDERALLY FUNDED RESEARCH

This invention was made with government support under grant AI31431 awarded by the National Institutes of Health. The government has certain rights in the invention.

BACKGROUND

Human monocytic ehrlichiosis (HME) caused by *Ehrlichia chaffeensis* was first reported in 1987. The clinical symptoms of HME include fever, headache, malaise, myalgia, rash, lymphadenopathy, and nausea (Rikihisa, 1999). Illness due to ehrlichiosis can be so mild that no medical care is sought, or the illness can be severe and sometimes fatal, particularly in the immune compromised and elderly. Symptoms are generally non-specific, and other diagnoses may be considered. Because the laboratory tests that detect ehrlichiosis are often not positive in the first week of illness, physicians base early patient treatment decisions on the signs and symptoms, as well as the patient's history of tick exposure. The physician also looks at specific blood tests to help determine the likelihood of ehrlichiosis. Clues such as a low platelet count (thrombocytopenia), abnormal white blood cell counts (decreased), or elevated liver enzyme levels are often helpful, yet non-specific predictors.

As yet there are no vaccines to protect against ehrlichiosis. Hence there is a need to develop a potential vaccine that can protect against *Ehrlichia* infection.

SUMMARY

Embodiments described herein demonstrate an *Ehrlichia* vaccine based on an *Ehrlichia* sonicate that provides protection against the pathogen at day 7 after *Ehrlichia* challenge. The present invention provides immunogenic compositions and vaccines, as well as therapeutic methods to prevent, ameliorate, or treat *Ehrlichia* infection or its sequelae.

Certain embodiments are direct to a vaccine composition comprising an immunizing amount of an *Ehrlichia* sonicate, wherein the *Ehrlichia* sonicate elicits a protective physiologic response. In certain aspects the *Ehrlichia* is one or more of *E. canis, E. chaffeensis, E. muris, E. ruminantium, E. ewingii*, and *E. ovis*. In a further aspect the sonicate can be a mixture of two or more sonicates or a sonicate of two or more *Ehrlichia*. In other aspects the composition can comprise an *Ehrlichia* sonicate and an adjuvant.

Other embodiments are directed to methods of vaccinating a subject against *Ehrlichia*, comprising administering the vaccine composition comprising an *Ehrlichia* sonicate as described herein to a subject. In certain aspects the subject has been identified as harboring *Ehrlichia*, is suspected of being exposed to *Ehrlichia*, has been bitten by an insect vector, or is exhibiting symptoms consistent with Ehrlichiosis. The method can further comprise administering 1, 2, 3, 4, 5, 6, 7, 8, or more doses over 1, 2, 3, 4, 5, 6, 7, 8, 9 days, weeks, or months. In certain aspects a subject is administered a first dose of *Ehrlichia* sonicate followed by a second dose administered at a later time.

A process for producing the vaccine composition comprising (a) growing *Ehrlichia* in a host cell; (b) inactivating the *Ehrlichia* by sonicating the *Ehrlichia*; (c) admixing the inactivated *Ehrlichia* with an adjuvant.

As used herein, "subject" refers to any species that can be infected by *Ehrlichia*. In certain embodiments the subject is a non-human animal subject. In particular embodiments the subject is either a human, bovine, equine, porcine, canine or a feline. In certain embodiments the animal subject is a canine or feline.

An "effective immunizing amount," as used herein, may vary depending upon the strain or strains of *Ehrlichia* used to generate the vaccine and may be any amount sufficient to evoke a protective immune response.

Although as used herein, a "protective immune response" can be an immune response in a subject that leads to protection against one or more indications of infection, a "protective immune response" does not require complete protection from any indication of infection. Rather, a "protective immune response" can be an immune response that is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection. The vaccines of the present invention are intended to provide a protective immune response.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
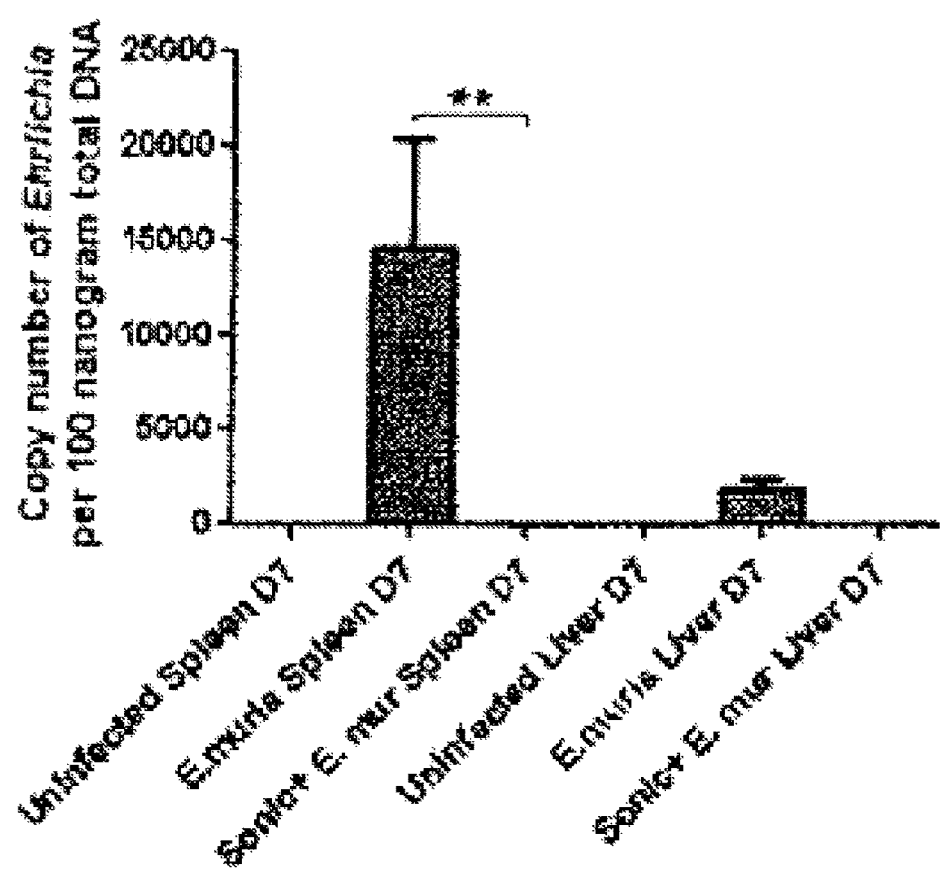
FIG. 1. Mice vaccinated with sonicated *E. muris* were protected against *E. muris* challenge. Spleen (p<0.01) and liver of mice vaccinated with sonicated *E. muris* had no bacteria on day 7 (n=3 per group) compared to unvaccinated mice as determined by quantitative real time RT-PCR.

The order Rickettsiales contains two families of arthropod-transmitted obligate intracellular bacteria that cause human diseases, including spotted fever rickettsiosis, typhus, scrub typhus, anaplasmosis, and ehrlichiosis. The genus *Ehrlichia* is a member of the family Anaplasmataceae, which also includes the genera *Anaplasma, Wolbachia*, and *Neorickettsia*. The *Ehrlichia* genus consists of six formally named members (*E. canis, E. chaffeensis, E. muris, E. ruminantium, E. ewingii*, and *E. ovis*). *E. chaffeensis* and *E. ewingii* are recognized as human zoonotic pathogens that also cause significant disease in the animal hosts (Breitschwerdt et al., 1998; Goldman et al., 1998).

Canine ehrlichiosis is a disease of dogs and wild canids (e.g., wolves) and is found worldwide. Canine ehrlichiosis is also known by other names such as 'tracker dog disease,' 'tropical canine pancytopenia,' canine hemorrhagic fever,' and 'canine typhus.' Canine monocytic ehrlichiosis (CME) is an important tick-borne disease of dogs worldwide that is caused primarily by the obligatory intracellular organism *Ehrlichia canis* (Neer et al., 2002). *E. canis*, the etiological agent of canine monocytic ehrlichiosis, is a globally distributed pathogen and has been recently associated with human infections (Perez et al. 2006). *E. chaffeensis* can also infect dogs and several wild animals (Dawson et al., 1996). Wild and domestic dogs with chronic infection serve as reservoir hosts. During the acute phase of infection, the clinical signs include fever, anorexia, and lymphadenopathy, and, in the chronic phase of infection, the dogs may show emaciation, hemorrhage, and peripheral edema (Buhles et al., 1974).

*Ehrlichia* were first associated with veterinary disease in Africa in 1925 by Cowdry, who identified *Ehrlichia ruminantium* in cattle. Ehrlichioses continue to be important veterinary diseases, but are now also associated with newly identified human tick-borne zoonoses (McBride and Walker, 2011). The obligate intracellular bacterium *Ehrlichia chaffeensis* that resides in mononuclear phagocytes is the etiologic agent of human monocytic ehrlichiosis (HME). HME is an emerging, highly prevalent, and often life threatening tick-transmitted infectious disease in the United States (Paddock and Childs, 2003; Walker et al., 2004; Walker, 2005). Ehrlichiosis is transmitted by the bite of infected ticks such as the lone star tick. The intracellular pathogen is transported through the host filopodium to neighboring cells (Thomas et al., 2010). Ehrlichiosis cannot be spread from person to person.

*E. ruminantium* is a veterinary pathogen that causes a severe acute infection known as heartwater in domestic ruminants localized primarily to sub-Saharan Africa (Uifenberg et al., 1983). Infection with the pathogen results in high mortality (50-90%). *E. ruminantium* is responsible for major production losses in African livestock industry and is also a potential danger to the U.S. livestock industry due to the presence of native tick vectors.

Vaccines are a low cost and effective strategy for the prevention and therapeutic reduction of infectious diseases. The inventors had earlier demonstrated that *Ehrlichia* Hsp60 and *Ehrlichia* p28-19 are diagnostic and vaccine candidates that can protect against *Ehrlichia* infection (Thomas and Walker 2009, 2011). The peptides, though very sensitive to detect *Ehrlichia* antibodies, would only mediate ehrlichial clearance on day 14 after ehrlichial challenge. This led to development a vaccine that provided stronger protection against *Ehrlichia* in the initial days of infection, which is described herein.

Embodiments described herein demonstrate an *Ehrlichia* vaccine that provides protection against the pathogen at day 7 after *Ehrlichia* challenge. The vaccine is based on sonicated *Ehrlichia* lysate, *Ehrlichia* sonicate. The sonicate is different from heat attenuated vaccines. Increase in temperature during heat inactivation can degrade some proteins and nucleic acids. Sonication does not destroy proteins, and nucleic acids including DNA or RNA. The DNA and RNA are fragmented into small sizes on sonication. The *Ehrlichia* (e.g., *E. muris*) sonicate can provide protection in a representative mouse model on day 7 after challenge with *E. muris*. The size of the spleen is enlarged (splenomegaly) during *Ehrlichia* infection. The spleen of mice vaccinated with sonicated *E. muris* lysate and later challenged with the pathogen did not exhibit splenomegaly on day 7 or 14. Mice vaccinated with sonicated *E. muris* lysate also had low levels of antibody production suggesting the absence of pathogen in the host. The low level of antibody isotypes in infected mice vaccinated with the sonicated *E. muris* lysate further suggests absence of the pathogen. It was also observed that sonicated lysate protected against the bacteria by an antibody independent mechanism.

The present invention provides immunogenic compositions and vaccines to prevent, ameliorate, or treat *Ehrlichia* infection or its sequelae. The present invention provides methods for the amelioration and/or prevention of *Ehrlichia* infection and related diseases or conditions in a subject by administering to the subject an immunogenic composition and/or a vaccine composition of the present invention. Thus, in one aspect the present invention provides an efficacious vaccine against *Ehrlichia*.

The present invention further provides methods and processes for producing an *Ehrlichia* sonicate for use in an immunogenic composition and/or vaccine. In particular embodiments the process comprises growing *Ehrlichia* in a cell or cell line to produce the source *Ehrlichia* for sonication, isolating the *Ehrlichia*, and subjecting the isolated *Ehrlichia* to sonication. In certain aspects the present invention includes a composition that comprises an inactive *Ehrlichia* sonicate. The immunogenic compositions and/or vaccines of the present invention can further include an adjuvant or other excipient.

The *Ehrlichia* lysates of the present invention can be produced from any number of *Ehrlichia* species or strains. In certain aspects the vaccine composition can comprise two or more *Ehrlichia* species and/or strains. The present invention includes an immunogenic composition for vaccinating a subject against ehrlichiosis.

*Ehrlichia* bacteria of the present invention can be grown on an appropriate cell and/or cell line. Examples of such cells and cell lines include primary cells (e.g., macrophage) and/or cell lines/continuous cell lines such as primary cell lines (blood macrophages or peritoneal macrophages); or continuous cell lines (human/dog hybrid cell line, canine macrophage cell line (DH-82), mouse peritoneal macrophage, Mouse/dog hybrid cell line (MDH-SP), mouse macrophage cell line, dog bone marrow cell line (DBM cells), feline embryonic fibroblast cell line (FEF), or tick cell lines (IDES and ISE6).

A cell culture infected with *Ehrlichia* may be grown in flasks, and subsequently passed to larger flasks to obtain larger volumes of material required to make immunogenic compositions and/or vaccines. Alternatively, the infected cell culture may be passed from flasks into subsequent roller bottles, spinner flasks, cell cubes, bioreactors, or any apparatus capable of growing cell culture on large scale in order to produce a suitable quantity of material required to blend an immunogenic composition and/or a vaccine. Infected cultures may be frozen down in a suitable media and used for infection of cell culture later.

Infection of the cell culture by *Ehrlichia* can be determined by several methods including, but not limited to, microscopic analysis of cells stained with dyes such as Giemsa stain, Cameo Difquick stain or acridine orange. In addition, antibodies specific for *Ehrlichia* can either be directly or indirectly labeled with fluorescent markers and viewed with a fluorescent light microscope and at a suitable wavelength for the particular fluorescent marker. Other techniques can be used to determine the level of infection of the culture including, but not limited to, quantitative polymerase chain reaction (qPCR) or PCR.

After isolation bacteria are subjected to ultrasound treatment, in other words, sound waves in a liquid at a frequency and intensity and for such duration as to rupture essentially all of the bacteria, without at the same time raising the temperature of the bacterial solution sufficiently to significantly denature components of the sonicated lysate. In certain aspects treatment in the liquid medium with sound waves at an appropriate frequency and of sufficiently high power level produces cavitation, whereby the structure of the bacteria in the liquid is disrupted and dispersed. The term "cavitation" defines a physical process whereby tiny bubbles present in the liquid are made to grow and collapse with great force. This occurrence produces violent pressure changes in the sonicated liquid at multiple microscopically spaced volume elements within the liquid. These pressure changes, which may be thousands of atmospheres in magnitude, break up any clusters of cells as well as disintegrate the cells themselves, if the cavitation is sufficiently intense, and shear their genetic material, deoxyribonucleic acid (DNA), or ribonucleic acid (RNA). The destructive force of the cavitation depends upon the surface tension of the sonicated liquid and the vapor pressure as well as the magnitude of the change in bubble size, which in turn depends upon the sound intensity and wave length. Other considerations include the effect of dissolved gases in the liquid and the control of temperature during the procedure.

In general, the frequency, intensity and duration of the sonication is to disintegrate the bacteria cells without raising the temperature of the liquid. In addition, the DNA or RNA of the bacteria which encodes their genetic information is sheared and is no longer capable of directing cellular replication. The completeness of the disruption of the cells can be determined by known methods including the use of microscopic examination and attempted growth of bacteria from the sonicated preparation.

As a general rule, the sonic waves are introduced into the liquid medium at a frequency of about 20 to about 40 kHz. The minimum intensity (power) of the sonic waves should be about 1 watt/cm$^2$ when utilizing a 20 kHz frequency. At this minimum level of power, cavitation is initiated. Preferably, the intensity level at about 20 kHz is 50 to 175 watts/cm$^2$. The destructive power of the sonic waves will vary as a function of the frequency of the sonic waves used, with a lower effect being produced at higher frequencies.

In the case of *Ehrlichia*, the cavitation intensity and frequency can be 20 kHz ranging from about 20 to about 150 watts/cm$^2$, or about 60-100 watts/cm$^2$. In certain aspect the samples can be pulsed for about 15 seconds at about setting 4-5 (about 25% of output of sonicator, available from Rx Technologies, Inc., Garden City, N.Y., U.S.A.) and then rested for about 60 seconds in an ice bath. The sample is further sonicated for an additional 3 pulses (about 15 seconds). In general, the duration of sonication may range from about 10 seconds to several minutes or longer and most preferably is performed in at least two installments for about 15 seconds or longer. The sonication duration and intensity schedule is provided which results in maximum lysis and removes any viable bacteria from the sonicate.

Other factors which affect the efficacy of the sonication include: temperature; static pressure; concentration of viruses, bacteria or cells in the liquid suspension; the type of liquid employed; the amount and types bacteria cells to be disintegrated; and duration of sonication as well as the amount and type of dissolved gases introduced into the liquid to achieve specific advantages during sonication.

In certain aspects the sonication is conducted at room pressure and the sample is maintained at a temperature of roughly about zero to 5° C. to avoid heating and to reduce the activity of cellular enzymes.

The duration of time the bacteria are sonicated will depend upon the bacteria. Typically the time will be sufficient to disrupt the bacteria so that virulent cells are minimized. For example, a gram of cultured cells may generally require about 3 minutes of sonication.

In certain aspects of the present invention, the immunogenic material is prepared by sonication. For sonication the samples can be placed into a stainless steel chamber in a physiologic buffer (PBS) and chilled on ice. Because of its infectious nature, the sample, in a sealed chamber, is generally attached to the sonicator horn (usually by thread means or some other method) and sonicated for a period sufficient to render the bacteria inactive without substantially affecting the ability of the sonicate to induce an immunogenic response.

After sonication of the bacteria the resulting product (a sonicate) is directly available for use as a vaccine. No further additions or purification of the resulting material is necessary. The sonicated vaccine can be injected as is, or for convenience of administration can be added to a pharmaceutically acceptable carrier or adjuvant. Suitable pharmaceutically acceptable carriers will be apparent to those skilled in the art, and include water and other polar substances, including lower molecular weight alkanols, polyalkanols such as ethylene glycol, polyethylene glycol (PEG), and propylene glycol as well as non-polar carriers.

Dosages of immunogenic material associated with adjuvants and/or carriers will often be about that of the immunogenic material (disrupted bacteria) alone. Of course, for use as human vaccines, dosages will be set by the prescribing physician considering relevant factors including the age, weight and condition of the patient and the pharmacokinetics of the agent and release characteristics of the agent from pharmaceutical dosage forms of the present invention.

In certain aspects of the present invention, the vaccine will generally contain an amount of protein ranging from about 25 micrograms to about 5 milligrams. Thus, the amount of protein used will fall within this range. The amount of protein contained in any sonicate can be generally assayed by the methods of Bradford, *Anal. Biochem.*, 72, 248 (1976) or Lowry, *J. Biol. Chem.*, 193, 265 (1951).

As indicated above, the immunogenic compositions and/or vaccines comprising an *Ehrlichia* sonicate of the present invention can, but do not necessarily further include one or more pharmaceutically acceptable adjuvants. Examples of pharmaceutically acceptable adjuvants are well known in the art, see, e.g. REMINGTON'S PHARMACEUTICAL SCIENCES, 18th Ed. (1990, Mack Publishing Co., Easton, Pa.) and GOODMAN AND GILMAN'S, THE PHARMACOLOGICAL BASIS OF THERAPEUTICS (10th ed. 2001).

In particular embodiments, the vaccine composition may comprise one or more pharmaceutically or veterinarily acceptable carrier or diluents. Non-limiting examples of carriers or diluents that may be used in vaccine composition formulations include water, glucose solutions, dextrose/saline, saline, phosphate buffered saline (PBS), HEPES buffer, Fischer's media, Hank's solution, and Ringer's solution. Such formulations may contain pharmaceutically acceptable auxiliary substances to enhance stability, deliverability or solubility, such as buffering agents, tonicity adjusting agents, wetting agents, detergents, and the like. Additives may also include additional active ingredients such as bactericidal agents or stabilizers. For example, the solution may contain thimerosal, gentamicin, sodium acetate, sodium lactate, sodium chloride, potassium chloride, calcium chloride, sorbitan monolaurate, or triethanolamine oleate. Compositions may be sterilized by conventional, known sterilization techniques.

In certain embodiments, it is contemplated the vaccine composition may further comprise other active components such as, but not limited to, an antipathogenic component directed against, or an antigenic component and/or attenuated and/or killed isolate of: rabies virus, Lyme disease (*Borrelia burgdorferi*), canine distemper virus, canine *bordetella*, canine parvovirus, canine adenovirus, canine coronavirus, *Babesia canis, Anaplasma phagocytophilum, Giardia; Leptospira interrogans* such as Serovars canicola, icterohaemorrhagiae, pomona, grippotyphosa or bratislava or the like, or any combination thereof.

In some embodiments, the vaccine and/or immunogenic composition may be formulated in a dosage unit form to facilitate administration and ensure uniformity of dosage. Herein, a dosage unit as it pertains to the vaccine composition refers to physically discrete units suitable as unitary dosages for a subject, each unit containing a predetermined quantity of *Ehrlichia* lysate calculated to produce the desired immunogenic effect in association with an adjuvant, carrier, and/or vehicle. In certain embodiments, the immunogenic composition and/or vaccine is lyophilized.

In certain embodiments the vaccine and/or immunogenic composition can be administered parenterally, for example, intramuscularly, subcutaneously, intraperitoneally, intradermally or the like, or the immunogenic composition and/or vaccine may be administered orally or intranasally in effective amounts according to a schedule determined by the time of potential exposure to a carrier of *Ehrlichia*. In this way, the treated subject may have time to build immunity prior to the natural exposure. In embodiments, more than one administration of the vaccine composition may be provided to a subject.

Vaccines of the present invention may be administered as a liquid, emulsion, dried powder, including as a lyophilized power, and/or in a mist through any parenteral route, intravenously, intraperitoneally, intradermally, by scarification, subcutaneously, intramuscularly, or inoculated by a mucosal route, e.g., orally, intranasally, as an aerosol, by eye drop, by in ovo administration, or implanted as a freeze dried powder.

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Materials and Methods:

Preparation of Vaccine and Immunization.

*E. muris* infected DH82 cells or spleen of mice infected with *E. muris* (day 7) were sonicated for 10 times in PBS buffer. Sonicated lysate was mixed with Freund's adjuvant (first dose) and injected into mice (200 microliter) (ip). The second dosage contained sonicated lysate mixed with Freund's incomplete adjuvant and injected two weeks later. Mice were challenged with *E. muris* (5000 bacteria) 15 days after the second immunization. Blood, spleen and liver were collected on days 7 and 14 for analysis.

Determination of Bacterial Load.

Ehrlichial copy numbers in vaccinated mice were determined by quantitative real time PCR method by analyzing the dsb gene (Stevenson et al., 2006).

Analysis of Serum.

To analyze the *Ehrlichia*-specific antibody response we coated p28-19 peptide on a Nunc MaxiSorp ELISA plate (1:250) and later incubated with the serum (1:100). Finally the antibodies were probed with goat anti-mouse lgG-alkaline phosphatase (AP) (1:500). For analysis of antibody isotypes, the Nunc MaxiSorp ELISA plates were coated with p28-19 peptides (1:250) and later incubated with the serum (1:100). Finally the antibodies were probed with goat anti-mouse (lgG1, lgG2a, lgG2b, lgG3, and lgM)-AP (1:350). After the addition of substrate the results were read on an ELISA reader.

B. Results

The inventors had earlier demonstrated that vaccination with *Ehrlichia* Hsp60 or p28-19 significantly reduces the bacterial load only on day 14 after bacterial challenge (Thomas and Walker, 2009, 2011). Mice vaccinated with the sonicated *E. muris* protected the host on day 7 after challenge with the pathogen as seen in the absence of bacterial load in the spleen and liver determined by quantitative real time PCR ($P<0.01$, as analyzed by one way ANOVA) (FIG. 1).

Figure 2:
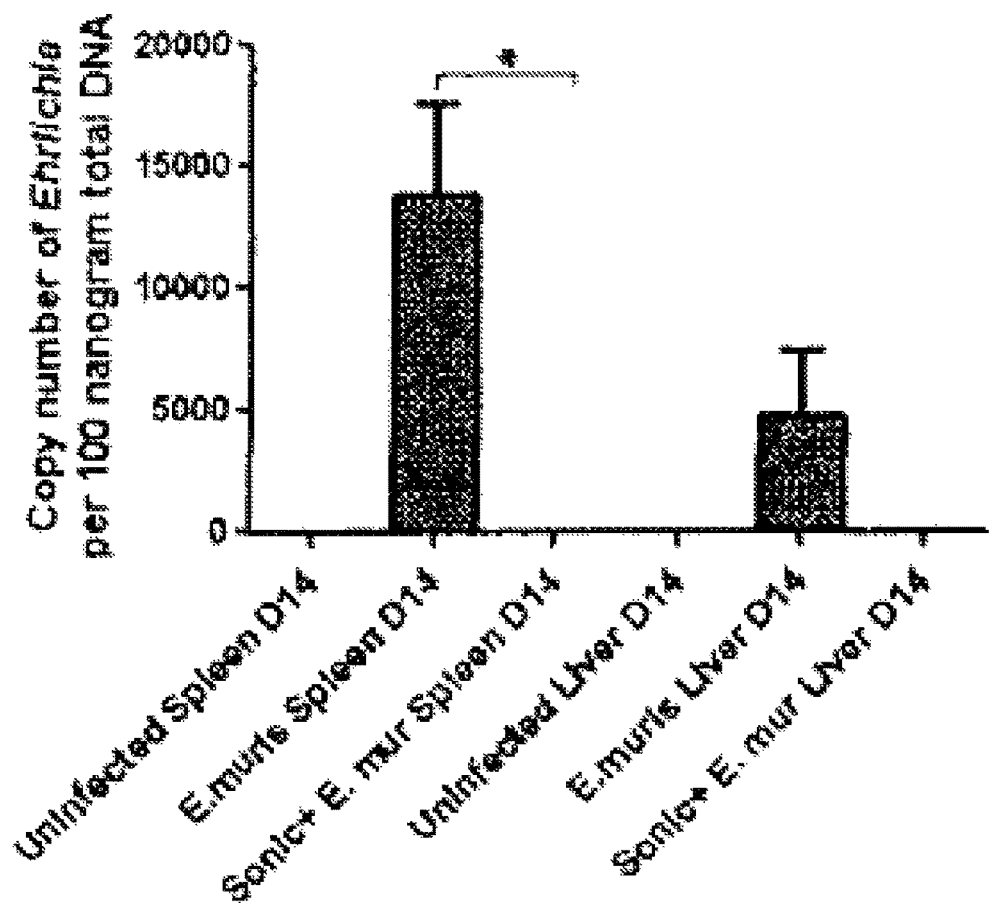
FIG. 2 Mice vaccinated with sonicated *E. muris* were protected against *E. muris* challenge. Spleen (p<0.05) and liver of mice vaccinated with sonicated *E. muris* had no bacteria on day 14 (n=3 per group) compared to unvaccinated mice as determined by quantitative real time RT-PCR.
Figure 3:
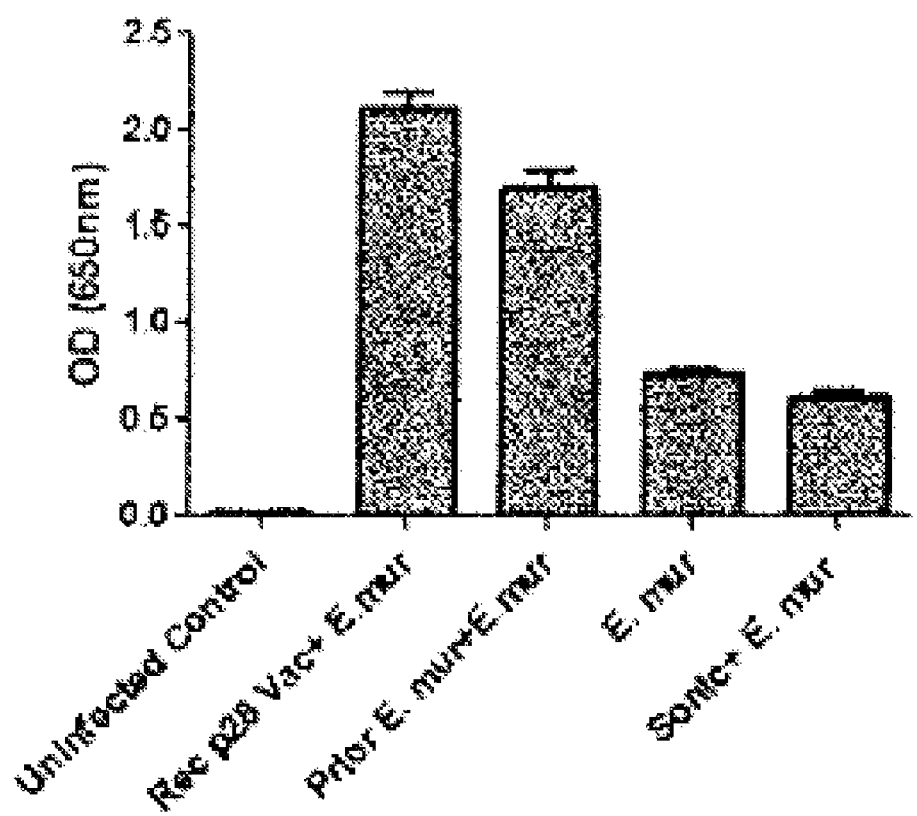
FIG. 3 Mice vaccinated with sonicated *E. muris* had low levels of *E. muris*-specific antibody. Mice immunized with sonicated *E. muris* and later challenged with the pathogen had the lowest antibody response, whereas mice vaccinated with recombinant p28-19 or infected with *E. muris* 2 months prior to challenge produced high levels of antibody as determined by ELISA.

The inventors also analyzed the bacterial load on day 14 after *E. muris* challenge. Mice immunized with the sonicated lysate also had no bacteria in the spleen and liver after *E. muris* challenge as determined by quantitative real time PCR ($P<0.01$, as analyzed by one way ANOVA)(FIG. 2). Prior experience with *Ehrlichia* vaccines had demonstrated that vaccinated mice produced high levels of *E. muris*-specific antibodies on day 14 after challenge. To determine whether antibody is responsible for clearance of *Ehrlichia* we performed a sandwich ELISA to probe for *Ehrlichia* specific antibody. Mice immunized with sonicated *E. muris* and later challenged with the pathogen had the lowest antibody response, whereas mice vaccinated with recombinant p28-19 or infected with *E. muris* two months prior to challenge produced high levels of antibody (FIG. 3).

Figure 4:
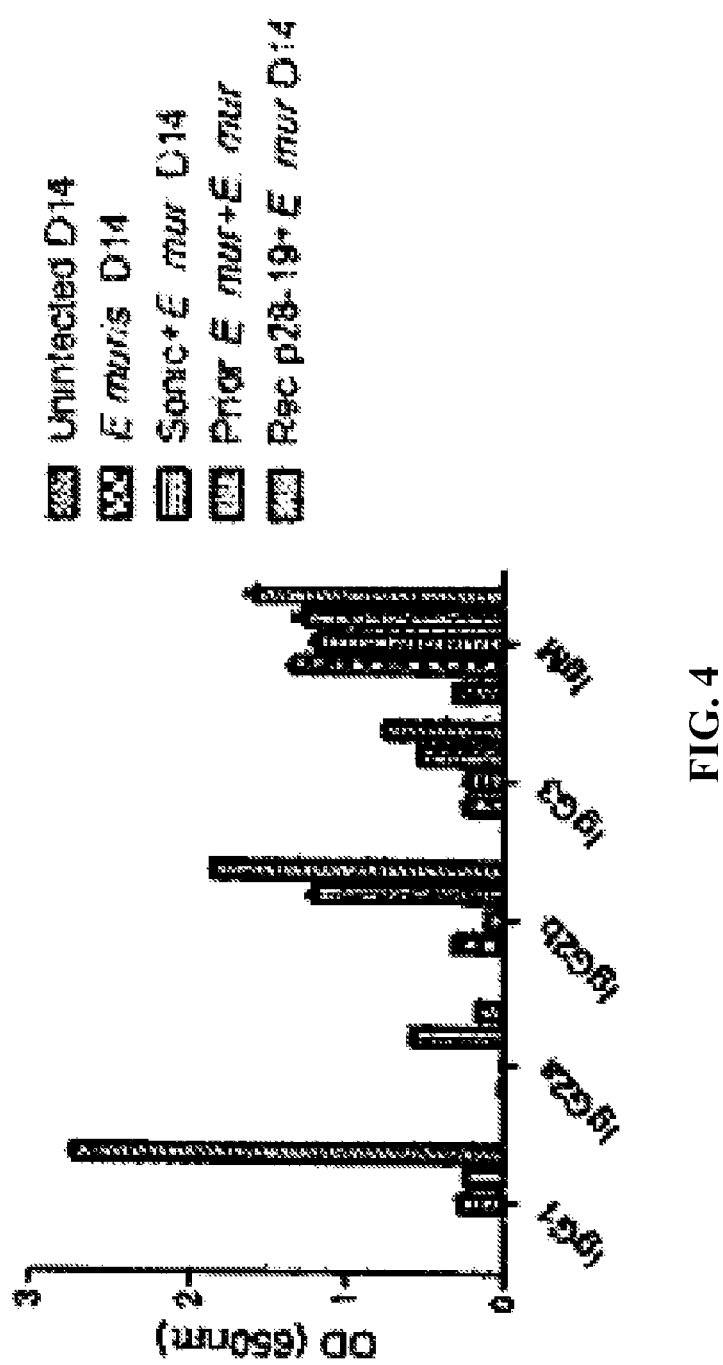
FIG. 4 Mice vaccinated with sonicated *E. muris* had low levels of *E. muris* specific antibody isotypes. Mice immunized with sonicated *E. muris* and later challenged with the pathogen had the lowest antibody isotypes, whereas mice vaccinated with recombinant p28-19 followed by challenging with the pathogen generated high levels of immunoglobulin isotypes as determined by ELISA.

Finally, the inventors determined the antibody isotypes in the serum from mice injected with sonicated *E. muris* and challenged with the pathogen. Mice vaccinated with sonicated *E. muris* and challenged with the pathogen had low levels of lgG1, lgG2b, and lgG3 compared to mice vaccinated with *Ehrlichia* p28-19 (FIG. 4).

The study demonstrates that sonicated *E. muris* lysate is a vaccine that provides strong protection against *Ehrlichia* infection.

REFERENCES

Breitschwerdt et al., *J Clin Microbial.* 1998, 36:2645-51.
Buhles et al., *J Infect Dis.* 1974, 130:357-67.
Dawson et al., *J Clin Microbial.* 1994, 32:2725-28.
Dawson et al., *Am J Vet Res.* 1996, 57:1175-79.
Goldman et al. *J Vet int Med.* 1998, 12:61-70.
Karpathy et al. *24th Meeting of ASR* 2010; Abstract 102.
Lockhart et al. *J Clin Microbial.* 1997, 35:1681-86.
McBride and Walker. *Expert Rev Mol Med.* 2011, 13:e3.
Neer et al., *J Vet Intern Med.* 2002, 16:309-15.
Paddock and Childs. *Clinical Microbial Rev.* 2003, 16:37-64.
Perez et al. *Ann NY Acad Sci.* 2006, 1078:110-17.
Rikihisa et al., *Microbes Infect.* 1999, 1:367-76.
Stevenson et al. *Infect lmmun.* 2006, 74:4856-64.
Sutton et al. *Immunol. Cell Biol.* 2000, 78:28-30.
Thomas et al. *Parasite Immunol.* 2009, 31:296-303.
Thomas et al. *PLoS One.* 2010, 5:e15775.
Thomas and Walker. 2009. Method of diagnosing and treating *Ehrlichia*. (U.S. patent application Ser. No. 61/281,178).
Thomas and Walker. 2011. Diagnosis and treatment of ehrlichiosis (U.S. patent application Ser. No. 61/462,277).
Uilenberg. *Adv. Vet. Sci. Comp. Med.* 1983, 27:427-80.
Walker. *Arch Virol Suppl.* 2005, 19:147-56.
Walker et al. *Trans Am Clin Climatol. Assoc.* 2004, 115: 375-82.

The invention claimed is:

1. A vaccine composition comprising an immunizing amount of an *Ehrlichia muris* sonicate, wherein the *Ehrlichia muris* sonicate elicits an antibody independent protective immune response within 7 days of *Ehrlichia muris* challenge.

2. The vaccine composition of claim 1, further comprising an adjuvant.

* * * * *